United States Patent [19]

Drauz et al.

[11] Patent Number: 6,037,474
[45] Date of Patent: Mar. 14, 2000

[54] PROCESS FOR THE PREPARATION OF CYCLIC 4-OXOAMIDINES

[75] Inventors: Karlheinz Drauz, Freigericht, Germany; Rolf Hoffmann, Brasschaat; Ivan Pilgrims, BE-Kontich, both of Belgium

[73] Assignee: Degussa-Huüls, Germany

[21] Appl. No.: 09/276,345

[22] Filed: Mar. 25, 1999

[30] Foreign Application Priority Data

Mar. 27, 1998 [DE] Germany .............................. 198 13 435

[51] Int. Cl.⁷ .................................................. C07D 235/02
[52] U.S. Cl. ...................................... 548/316.4; 548/326.1
[58] Field of Search ............................... 548/316.4, 326.1

[56] References Cited

U.S. PATENT DOCUMENTS

| | | | |
|---|---|---|---|
| 2,602,799 | 7/1952 | Goldberg et al. | 548/316.4 |
| 4,280,008 | 7/1981 | Schoellkopf et al. | 548/316.4 |
| 5,698,704 | 12/1997 | Jackson | 548/300.7 |
| 5,910,595 | 6/1999 | Durrwachter | 548/300.7 |

FOREIGN PATENT DOCUMENTS 1202299  8/1970  United Kingdom ................ 548/316.4

OTHER PUBLICATIONS

Wiering et al, Recuiel De Travaux Chemique, vol. III, pp. 284 to 288 (1971).

*Primary Examiner*—Floyd D. Higel
*Attorney, Agent, or Firm*—Omri M. Behr, Esq.

[57] ABSTRACT

The present invention relates to a process for the preparation of cyclic 4-oxoamidines. Such substances are precursors of active substances having biological action. The process according to the invention forms a further method of obtaining this class of compound.

By reacting condensation products of aldehydes and aminonitriles or amino acid amides with oxidizing agents, the desired cyclic 4-oxoamidines are obtained according to the invention in good to very good yields.

25 Claims, No Drawings

PROCESS FOR THE PREPARATION OF CYCLIC 4-OXOAMIDINES

FIELD OF THE INVENTION

The present invention relates to a process for the preparation of cyclic 4-oxoamidines of the general formula I.

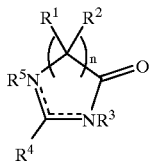
(I)

Compounds of this type are important intermediates for the synthesis of active substances having biological action, such as, for example, antihypertensives or plant-protecting compositions.

DISCUSSION OF THE PRIOR ART

Hitherto, compounds of the general formula I have been obtained from acylated α-aminonitriles by hydrolysis of the nitrile group to the carbamoyl group and subsequent base-catalysed cyclisation (U.S. Pat. No. 5,424,450).

In the recently published Offenlegungsschrift EP 0 789 019, the corresponding acylated α-aminonitrile is cyclised directly to the corresponding 4-oxoimidazolinium salt in the presence of an alcohol under acid conditions.

SUMMARY OF THE INVENTION

The object of the present invention is to provide a further process for the preparation of the compounds of the general formula I.

By preparing amidines of formula I or their salts

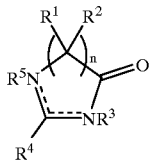
(I)

wherein $R^1$ and $R^2$ may be the same or different and represent H, $(C_1-C_8)$-alkyl, $(C_2-C_8)$-alkenyl, $(C_2-C_8)$-alkynyl, $(C_1-C_8)$-alkoxy, $(C_2-C_8)$-alkoxyalkyl, which may optionally be linear or branched and may optionally be mono- or poly-substituted by halogens, radicals containing N, O, P atoms.

Particularly preferred as heterosubstituted substituted alkyls are:

1-, 2-, 3-, 4-Halo-$(C_1-C_4)$-Alkyls, such as Chloromethyl, 2-Chlorethyl,2-,3-Chloropropyl, 2-, 3-, 4-Chlorobutyl, Fluoromethyl, 2-Fluorethyl, 2-,3-Fluoropropyl, 2-, 3-, 4-Fluorobutyl, Bromomethyl, 2-Bromethyl, 2-,3-Bromopropyl, 2-, 3-, 4-Bromobutyl; protected 1-, 2-, 3-, 4-Amino-$(C_1-C_4)$-Alkyls, such as Aminomethyl, 2-Aminoethyl, 2-, 3-Aminopropyl, 2-, 3-, 4- Aminobutyl; protected 1-, 2-, 3-, 4-Hydroxy-$(C_1-C_4)$-Alkyl, wie Hydroxymethyl, 2-Hydroxyethyl, 2-,3-Hydroxypropyl, 2-, 3-, 4-Hydroxybutyl; 1-, 2-, 3-, 4-Diarylphosphin-$(C_1-C_4)$-Alkyls such as Diphenylphosphinomethyl, 2-Diphenylphosphinethyl, 2-,3-Diphenylphosphinopropyl, 2-, 3-, 4-Diphenylphosphinobutyl.

The protecting groups for amino containing $R^1$ and $R^2$ groups include Z-, Boc-, Formyl, Acetyl, methoxycarbonyl, and Ethoxycarbonyl and the like. The protecting groups for hydroxy containing $R^1$ and $R^2$ groups include Methyl, Benzyl, Methoxymethyl, 1,2-Ethoxyethyl, Methoxyethyl and Tetrahydropyranyl and the like.

$(C_3-C_7)$-cycloalkyl, which may be saturated and/or unsaturated and may be mono- or poly-substituted by linear or branched $(C_1-C_8)$-alkyl, $(C_3-C_7)$-cycloalkyl, which may be saturated and/or unsaturated and may be mono- or poly-substituted by linear or branched $(C_1-C_8)$-alkyl, $(C_2-C_8)$-alkenyl, $(C_1-C_8)$-alkoxy, $(C_2-C_8)$-alkoxyalkyl, halogens and radicals containing N, O, P atoms, or may contain hetero atoms such as N, O, P in the ring, suitably 1-, 2-, 3-, 4-Piperidyl, 1-, 2-, 3-Pyrrolidinyl, 2-, 3-Tetrahydrofuryl, 2-, 3-, 4-Morpholinyl aryl, such as phenyl and/or naphthyl, aralkyl, such as benzyl and/or phenethyl, heteroaryl, such as furyl, pyrrolyl, pyridyl, suitably 1-, 2-, 3-Furyl, such as 1-, 2-, 3-Pyrrolyl, 1-,2-,3-Thienyl, 2-, 3-, 4-Pyridyl, 2-, 3-, 4-, 5-, 6-, 7-Indolyl, 3-, 4-, 5-Pyrazolyl, 2-,4-, 5-Imidazolyl, Acridinyl, Quinonolinyl, Phenanthridinyl, 2-, 4-, 5-, 6-Pyrimidinyl.

heteroaralkyl, such as furfuryl, pyrrolylmethyl, pyridylmethyl, furylethyl, pyrrolylethyl, pyridylethyl, wherein the rings just mentioned may optionally be mono- or poly-substituted by linear or branched $(C_1-C_8)$-alkyl, $(C_2-C_8)$-alkenyl, $(C_1-C_8)$-alkoxy, $(C_2-C_8)$-alkoxyalkyl, halogens, radicals containing N, O, P atoms, or $R^1$ and $R^2$ may be bonded together as shown by the phantom link between them whereby, together with the carbon atom to which they are each attached, they form a 3- to 7-membered carbocyclic or heterocyclic, saturated or unsaturated ring, which may optionally be mono- or poly-substituted by linear or branched $(C_1-C_8)$-alkyl, $(C_2-C_8)$-alkenyl, $(C_1-C_8)$-alkoxy, $(C_2-C_8)$-alkoxyalkyl, halogens, radicals containing N, O, P atoms, $R^3, R^4, R^5$, each independently of the others, may have the meanings given for $R^1$, with the proviso that $R^3$ and $R^5$ may not simultaneously be other than H and the radicals of the group $R^3$, $R^4$ or $R^5$ are not bonded together to form a ring, n is an integer from 1 to 3, by oxidising rings of the general formula II

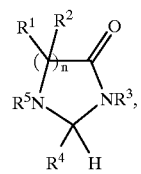
(II)

wherein the radicals $R^1$ to $R^5$ and n have the meanings given above, extremely pure compounds of the general formula I are advantageously obtained in good to very good yields.

The Group

may be represented in any of the following three embodiments, namely

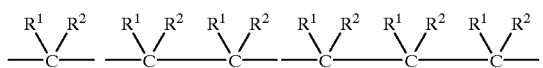

The compounds of the general formula II can be prepared by methods known per se (Journal für prakt. Chemie, Vol. 32b, No. 2, 1984, p. 279–286; Bull. Chem. Soc. Jpn., 1971, 44, 3445–3450). It is, however, preferred to prepare such rings by the condensation of α-aminonitriles or α-amino acid amides with aldehydes. The required α-aminonitriles can be obtained analogously to a Strecker synthesis; the α-amino acid amides are formed from the corresponding α-aminonitriles by hydrolysis.

The subsequent oxidation of the aminals can be carried out by methods known to the person skilled in the art. Halogens or halogen derivatives are advantageously used as oxidising agents. The compounds chlorine, bromine and iodine are advantageously used as halogens for the oxidation. Suitable halogen derivatives are, for example, hypochlorite, chlorite, dichlorooxide, tert-butyl hypochlorite, methyl hypochlorite, trichloroisocyanurate, dichloroisocyanurate, chloramine T, N-chlorosuccinimide, 1,3-dichloro-5,5-dimethylhydantoin, 1-chloro-3-bromo-5,5-dimethylhydantoin, N-chlorosuccinimide, hypobromite, bromate/bromide, bromochloride, 1,3-dibromo-5,5-dimethylhydantoin, 1-chloro-3-bromodimethylhydantoin, N-bromosuccinimide, methyl hypobromite, etc.. Elemental chlorine is especially preferred. However, the oxidation of compounds of the general formula II using agents from the group of the compounds containing active oxygen is also preferred. There come into consideration as such substances, inter alia, hydrogen peroxide, Caro's acid, etc.. Very special preference is given to the use of $H_2O_2$ or its derivatives having an oxidising action, such as $Na_2O_2$, tert-BuOOH, $RCO_3H$, etc.

Electrochemical oxidising processes, such as are known, for example, from Tetrahedron 1989, 45, 1691 ff, may also be employed for the oxidation of the corresponding cyclic 4-oxoaminals to 4-oxoamidines. With the aid of a mediator, therefore, nitrogen atoms in the molecule are substituted with application of a voltage. Elimination to conclude the process produces the desired amidines. An electrochemical cell which can be used for that purpose can be taken from the prior art. Suitable mediators are in principle any mediators familiar to the person skilled in the art. Very special preference is given to the use of chloride ions.

Agents from group VIII of the noble metals, such as, for example, Ru, Rh, Pd, Os, Ir, Pt, may likewise be used for the oxidation. Those metals, which are to be used in substoichiometric amounts preferably on customary support materials (such as, for example, carbon, $Al_2O_3$, $SiO_2$, carbonates or oxides), lead to dehydrogenation of the compounds of the general formula II. Very special preference is given to the use of palladium for the dehydrogenation. Similar dehydrogenations of amines have already been described by Murahashi et al. (J. Am. Chem. Soc. 1983, 105, 5002–5011).

There is preferably oxidised or dehydrogenated a compound wherein n=1, the radicals $R^1$ and $R^2$ are bonded together via their linking carbon atom to form a 5-membered carbocyclic ring, and $R^3$ and $R^5$ are both H and $R^4$ is a linear butyl radical. Such a molecule forms the precursor for the preparation of the angiotensin II antagonist Irbesartan® (Drugs of the Future 1997, 22, 481–491).

The dehydrogenation is preferably carried out in an organic solvent from the group of the ketones, ethers, esters, carboxylic acid amide (DMF, N-methylpyrolidinone), alkanes, cycloalkanes, halogenated hydrocarbons, or mixtures thereof, with special preference being given to a solvent from the group of the ketones, especially MIBK.

The temperature range of the reaction is from 50° C. to 250° C., preferably from 90° C. to 180° C., especially from 100° C. to 140° C.

The metal required for the dehydrogenation is used in the range of from 0.1 wt. % to 10 wt. %, preferably from 0.5 wt. % to 7 wt. %, especially 3 wt. %, relative to the compound to be dehydrogenated. The metal is used on supports, preferably on activated carbon.

The preparation of the compounds of the general formula I is advantageously effected by crystallisation in the form of a salt. There may be used for the salt formation in principle any inorganic and organic acids known to the person skilled in the art, such as, for example, HCl, HBr, $RSO_3H$, $HCO_2H$, $(HOOC)_2$, $HClO_4$, $H_2SO_4$, $HBF_4$, $H_3PO_4$, $CF_3CO_2$4, p-TosOH. Crystallisation in the form of the hydrochlorides is preferred.

The scheme below describes again the preparation of the cyclic 4-oxoamidines for the compounds wherein n=1 and $R^3$, $R^5$=H.

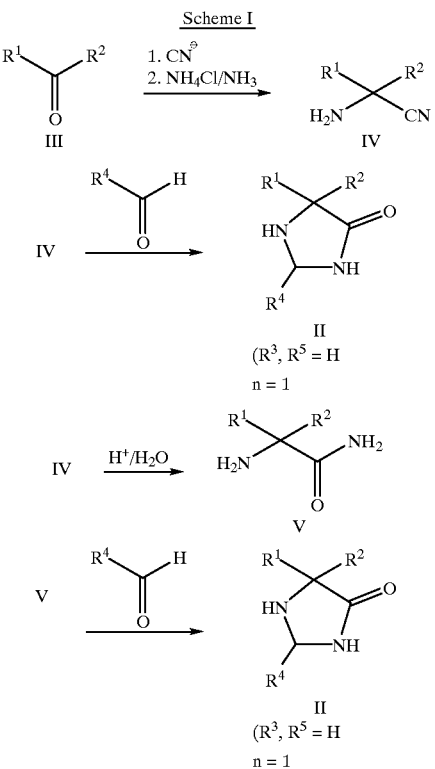

Scheme I

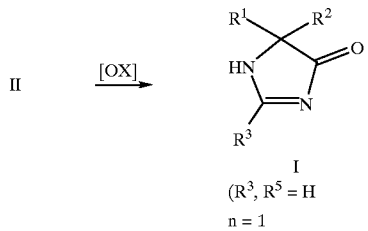

(R³, R⁵ = H
n = 1

[OX] = a) peroxide oxidation, b)dehydrogenation, c)halogen oxidation, d)electrochemical oxidation.

For the preparation of higher homologous ring systems, the person skilled in the art preferably uses β- or γ-aminonitriles as starting materials. Those compounds can likewise be prepared by the methods known to the person skilled in the art (lit.: J. prakt. Chem. 1984, 326, 279–286).

There come into consideration as linear or branched ($C_1$–$C_8$)-alkyl radicals methyl, ethyl, n-propyl, isopropyl, n-butyl, isobutyl, sec-butyl, tert-butyl, pentyl, hexyl, heptyl or octyl, as well as all the isomers of constitution. The linear or branched ($C_2$–$C_8$)-alkenyl radical includes all substituents listed above in connection with the ($C_1$–$C_8$)-alkyl radical with the exception of the methyl radical, there being at least one double bond present in those radicals. The scope of ($C_2$–$C_8$)-alkynyl corresponds to that of ($C_2$–$C_8$)-alkenyl, but at least one triple bond must be present in that case. The ($C_1$–$C_8$)-alkoxy radical corresponds to the ($C_1$–$C_8$)-alkyl radical, with the proviso that it is bonded to the ring via an oxygen atom. ($C_2$–$C_8$)-Alkoxyalkyl is to be understood as meaning radicals in which the alkyl chain is interrupted by at least one oxygen function, wherein two oxygen atoms may not be bonded together. The number of carbon atoms indicates the total number of carbon atoms contained in the radical. Radicals containing N, O, P atoms are especially alkyl, alkenyl, alkynyl radicals of the type mentioned above which have one or more of those hetero atoms in their chain or are bonded to the amidine via one of those hetero atoms. ($C_3$–$C_7$)-Cycloalkyl is to be understood as being cyclopropyl, cyclobutyl, cyclopentyl, cyclohexyl or cycloheptyl radicals.

The protecting groups for amino and hydroxy containing $R^1$ and $R^2$ groups are those mentioned in Chemical Synthesis of Peptides, G. Jones, Oxford Science Publication 1991 and Protective Groups in Organic Synthesis, T. W. Green, Wiley, N.Y. 1991, respectively, which are incorporated by reference.

The Examples which follow are intended to explain the invention without limiting it in any way.

EXAMPLE 1a

Preparation of 1-aminocyclopentyinitrile (ACCN)

193 g of cyclopentanonecyanhydrin (max. 1.74 mol.) are added dropwise in the course of 45 minutes, while cooling at 15° C., to a solution of 250 g of $NH_3$(25%; 3.67 mol.). The reaction mixture is heated to 50° C. in the course of 45 minutes and maintained at that temperature for 5.5 hours. The mixture is cooled to 25–30° C. and then extracted using 300 ml of MTBE. The organic phase is separated off and the solvent is evaporated off at 50° C. (25–30 mbar). 147 g of 1-aminocyclopentyinitrile (90%; GC) are obtained, corresponding to a yield of 69% of the theoretical yield.

EXAMPLE 1b 150 g of cyclopentanonecyanhydrin (max. 1.35 mol.) are added at 35° C., in the course of 45 minutes, to a solution of 45 g of $NH_4Cl$ in 200 g of $NH_3$ (25%, 2.94 mol.). A further 43 g of $NH_4Cl$ are then added and the reaction mixture is stirred for 1.5 hours at 45° C. The mixture is then cooled to room temperature and the organic phase is separated off. 120 g of 1-aminocyclopentyinitrile (86% titration; 94% GC) are obtained, corresponding to a yield of 69% of the theoretical yield.

EXAMPLE 2

Preparation of 1-aminocyclopentylcarboxamide (ACCA)

215 ml of sulfuric acid (96–98%) are placed in a vessel and pre-heated to 60° C. In the course of 60 minutes, 125 g of 1-aminocyclopentyinitrile (85%; 0.965 mol.) are added thereto. The reaction mixture is stirred for 60 minutes at 60° C. and for a further 60 minutes at 80° C. The reaction mixture is added at 40–45° C. to 500 g of $NH_3$ (25%) and 300 g of $H_2O$. The mixture is then extracted six times using 500 ml of MIBK each time, and the combined organic phases are concentrated to the greatest possible extent on a rotary evaporator. The solution is cooled to 4° C. and the crystals are filtered off. After drying, 96 g of 1-aminocyclopentyl-carboxamide (98.2%; HPLC) are obtained, corresponding to 76.2% of the theoretical yield.

EXAMPLE 3

Preparation of 2-butyl-1,3-diaza-spiro[4.4]nonan-4-one (DSPC)

Ammonia solution (20%; 20 g, 0.30 mol.) is added to a solution of 126 g of 1-aminocyclopentanecarboxamide (>98%, 0.98 mol.) in 150 g of water. 86 g of valeraldehyde (0.99 mol.) are then added at 15° C., during which the temperature rises to 32° C. The reaction mixture is heated to 70° C. and stirred for 7 hours at that temperature. 350 ml of MIBK are added to the emulsion, and the mixture is cooled, with stirring, and the organic phase is separated off. The extract is extensively concentrated by evaporation (200 g), and 200 g of n-hexane are added, and the crystals are filtered off. After drying there remain 125 g of 2-butyl-1,3-diaza-spiro [4.4]nonan4-one (HPLC: 98.6%).

The hexane phase is concentrated to about ⅔ and cooled to 15° C. A further 22 g of product are isolated, corresponding to a yield of 73% of the theoretical yield.

$^1$H-NMR (500 MHz, DMSO-$d_6$): δ=0.90 ppm (t, 3-H), 1.20–1.70 (m, 14-H), 1.80–1.95 (m, 1-H), 4.30 (t, 1-H), 8.20 (s, 1-H).

$^{13}$C-NMR (125 MHz, DMSO-$d_6$): δ=18.8 ppm, 22.0, 24.7, 26.4, 36.0, 36.2, 36.9, 67.5, 68.1, 179.9.

$M^+$=197

EXAMPLE 4

Preparation of 2-butyl-1,3-diaza-spiro[4.4]nonan-4-one (DSPC)

100 g of cyclopentanonecyanhydrin (max. 0.90 mol.) are added at a temperature of 35° C., while passing in $NH_3$, to a solution of 245 g of a solution of $NH_3$ (17.8 wt. %, 2.56 mol.) containing 10 wt. % ACCN (24.6 g; 0.223 mol.). The mixture is stirred for one hour at 40° C., and then the aqueous phase (264 g) is separated off. The organic phase is dissolved in 200 ml of MeOH, and 1.6 ml of NaOH (50%) are added thereto at 10–20° C. 90 g of valeraldehyde (1.03 mol.) and 2×0.8 ml of NaOH (50%) are then added, the temperature being maintained at 10–20° C. The temperature is then raised to 60° C. and the mixture is stirred for 2 hours at that temperature. 352 g of reaction mixture containing 40.2 wt. % (HPLC, 141.5 g, 0.721 mol.) of DSPC are obtained, corresponding to a yield of 80.2% in relation to cyclopentanonecyanhydrin.

EXAMPLE 5

Preparation of 2-butyl-1,3-diaza-spiro[4.4]nonen-4-one×HCl (SPC) (Dehydrogenation with Pd/C)

130 g of a reaction mixture containing 29.6 g of 2-butyl-1,3-diaza-spiro 4.4]nonan-4-one (0.151 mol.) in methanol are diluted with 80 g of MIBK, and 47 g of HCl in isopropanol (15.4%, 0.204 mol.) are added thereto at 90° C. in the course of 30 minutes. The suspension is cooled to 30° C. and filtered and washed with MIBK. The filter cake is suspended in 100 g of MIBK and adjusted to pH 7.5 at 90° C. using 14 ml of $NH_3$ solution (25%; 0.166 mol.).

The aqueous phase is separated off and the organic phase is subjected to azeotropic dehydration (7 g of distillate).

10 g of Pd/C are added to the MIBK solution, and the mixture is heated for 12 hours under reflux. The catalyst is filtered off while warm, and a solution of 47 g of HCl in isopropanol (15.4%; 0.204 mol.) is added at 90° C. to the filtrate. The suspension is cooled to 25° C., washed with approximately 40 g of MIBK and dried. 26 g (99%; HPLC; >95% NMR) are obtained, corresponding to a yield of 74% of the theoretical yield.

$^1$H-NMR (500 MHz, DMSO-$d_6$): δ=0.90 ppm (t, 3-H) 1.32 (sex, 2-H), 1.65–2.05 (m, 10-H), 2.78 (t, 2-H), 13.1–14.0 (m, 2-H).

$^{13}$C-NMR (125 MHz, DMSO-$d_6$): δ=13.28 ppm, 21.35, 24.88, 26.54, 27.23, 36.43, 72.03, 173.18, 179.49.

EXAMPLE 6

Preparation of 2-butyl-1,3-diaza-spiro[4.4]nonen-4-one×HCl (SPC) (Oxidation with Chlorine)

a) A solution of 36 g of DSPC (0.18 mol.) in 128 g of MeOH is mixed with 22 g of $Na_2CO_3$ (0.21 mol.), are added thereto at a temperature of 5–10° C. and 30 g of chlorine (0.42 mol.) passed in. Stirring is then carried out for one hour at 10–15° C., and the suspension is filtered. The filtrate is heated for 2 hours at 60° C. and then cooled to 20° C. The resulting solid is filtered off and dried. 11 g of SPC (94.6% HPLC) are obtained. The mother liquor is extensively concentrated and the residue is stirred with 150 g of MIBK. After filtration and drying, a further 15 g of SPC×HCl (93.5% HPLC) are obtained, corresponding to a yield of 51 % of the theoretical yield.

b) 176 g of a DSPC reaction solution (46.1 wt. %; 0.41 mol.) are concentrated in vacuo at 70° C. (20 mbar). The residue is dissolved in 324 g of MeOH and mixed with 45 g of $Na_2CO_3$ (0.42 mol.). A total of 79 g of chlorine (1.11 mol.) is then passed in at 10° C., and the reaction mixture is subsequently stirred for one hour at 20° C. The solid is removed from the suspension by filtration, and the filtrate is heated at 60° C. for one hour. MeOH is then distilled off in vacuo, and 600 g of MIBK are added. Methonol is distilled off completely by distillation to 115° C., and the resulting solid is filtered off and dried. 83 g of SPC×HCl (91% HPLC) are obtained, corresponding to a yield of 79.5% of the theoretical yield.

c) 150 g of a DSPC reaction solution (35.4%, 53 g, 0.27 mol.) are concentrated in vacuo at 70° C. (20 mbar), and the residue is taken up in 220 g of MeOH. 50 g of $Na_2CO_3$ (0.47 mol.) are added, and 75 g of chlorine (1.05 mol.) are passed in at a temperature of 10° C. The suspension is filtered and the filtrate is heated to 60° C. A further 125 g of MeOH are added, and the reaction mixture is stirred for 3 hours at that temperature. The solvent is distilled off to the greatest possible extent, and 500 g of MIBK are added to the residue. The suspension is freed of MeOH residues (T=115° C.) and the solid is filtered off. After drying, 53 g of SPC×HCl (89% HPLC) were obtained, corresponding to a yield of 76% of the theoretical yield.

EXAMPLE 7

Preparation of 2-butyl-1,3-diaza-spiro[4.4]nonen-4-one×HCl (SPC) (Complete Run-through of the Process)

1.4 ml of triethylamine are added to 475 g of cyclopentanone (5.64 mol.), and the mixture is cooled to 20° C. 152.5 g of HCN (5.64 mol.) are added thereto with cooling in the course of one hour, in such a manner that the reaction temperature is<20° C. The reaction mixture is stirred for a further 60 minutes at 30° C. and cooled to room temperature. The pH is then adjusted to 1 by the addition of 0.5 ml of $H_2SO_4$ (96–98%). The cyanhydrin is used in aliquot form for the further reactions.

5 g of $NH_4Cl$ are added to a solution of 240 g of amination aqueous phase. 100 g of cyclopentanonecyanhydrin (max. 0.90 mol.) are added thereto, while passing in $NH_3$ whereupon the temperature rises to 35° C. After 90 minutes at 40° C., the lower aqueous phase is separated off. 200 ml of methanol and 1.6 ml of NaOH (50%) are placed in a vessel, and the organic phase and 90 g of valeraldehyde (1.03 mol.) are added thereto simultaneously in such a manner that the reaction temperature is maintained at 10–20° C. After the addition of 45 g and 90 g of valeraldehyde, a further 0.8 ml of NaOH (50%) is added. The reaction mixture is then heated for 2 hours at 60° C. 357 g of a solution containing 41.8 wt. % of 2-butyl-1,3-diaza-spiro[4.4]nonan-4-one (HPLC, 149.2 g, 0.760 mol.) are obtained. The solution was concentrated (70° C., 25 mbar) and the residue was dissolved in 600 g of MIBK.

A solution of 99.5 g of DSPC (max. 0.507 mol.) in 400 g of MIBK is diluted at 85° C. with 100 g of a solution of HCl in isopropanol (25.5%, 0.70 mol.) and with 150 g of isopropanol. The precipitate is filtered off and washed with MIBK.

The filter cake is suspended in 720 g of MIBK and stirred at 85° C. with 100 ml of $H_2O$ and 56 g of NaOH (50%, 0.70 mol.) to complete the reaction. The aqueous phase is separated off and the organic phase is subjected to azeotropic dehydration. 327 g of distillate to 115° C. were removed. 48 g of catalyst are then added and the reaction mixture is heated for 8 hours under reflux. The catalyst was filtered off and the filtrate was adjusted from pH 7 to pH 0 using 85 g of HCl (32%, 0.75 mol.).

The suspension is then subjected to azeotropic distillation to a head temperature of 114° C. (75 g of $H_2O$). The suspension is filtered and the filter cake is dried. 107 g (>95% NMR, 0.440 mol.) of 2-butyl-1,3-diaza-spiro [4.4] nonan-4-one×HCl are obtained, corresponding to a yield of 73%, based on cyclopentanonecyanhydrin.

EXAMPLE 8

Preparation of 2-butyl-4-methyl-4-(2-methylethyl)-imidazolidin-5-one 20.0 g of 2-amino-2,3-dimethylbutyramide (>96%, 0.147 mol.) are dissolved at room temperature in 100 ml of $H_2O$ and 50 ml of methanol and mixed with 13.2 g of valeraldehyde (0.152 mol.). The mixture is heated for 2.5 hours at 70° C. The two-phase mixture is extracted three times at room temperature using 200 ml of MIBK each time, and the combined organic phases are concentrated in vacuo. 25.3 g (97.8% (cis/trans mixture: 25:72; no assignment) of a white solid were obtained, corresponding to a yield of 82% of the theoretical yield.

EXAMPLE 9

Preparation of 2-butyl-4-methyl-4-(methylethyl)-1H-imidazol-5(4H)-one×HCl

A 20% solution of 2-butyl-4-methyl-4-(2-methylethyl)-imidazolidin-5-one in MIBK is mixed with Pd/C and heated for 12 hours under reflux. The catalyst is then filtered off and the filtrate is reacted with HCl in isopropanol. The resulting solid is filtered off and dried (purity>95% NMR).

$^1$H-NMR (500 MHz, DMSO-d$_6$): □=0.82 ppm (d, 3-H), 0.92 (t, 3-H), 1.00 (d, 3-H) 1.35 (sex, 2-H), 1.42 (s, 3-H), 2.80–2.95 (m, 2-H), 13.2–14.0 (m, 2-H).

EXAMPLE 10

Preparation of 2-butyl-1,3-diaza-spiro[4.4]nonen-4-one (SPC) (Oxidation of the Reaction Solution with Chlorine)

176 g of a DSPC reaction solution (46.1 wt. %; 0.41 mol.) are concentrated in vacuo at 70° C. (20 mbar). The residue is dissolved in 324 g of MeOH and mixed with 45 g of Na$_2$CO$_3$ (0.42 mol.). A total of 79 g of chlorine (1.11 mol.) is then passed in at 10° C., and the reaction mixture is subsequently stirred for one hour at 20° C. The solid is removed from the suspension by filtration, and the filtrate is heated at 60° C. for one hour. MeOH is then distilled off in vacuo, and 600 g of MIBK are added. Methanol is distilled off completely by distillation to 115° C., and the resulting solid is filtered off and dried. 83 g of SPC (91% HPLC) are obtained, corresponding to a yield of 79.5% of the theoretical yield.

We claim:

1. Process for the preparation of a cyclic 4-oxoamidine of the formula I

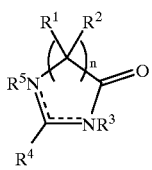

(I)

or addition salts thereof with organic and inorganic acids wherein $R^1$ and $R^2$ may be the same or different represent:
H,
linear or branched chain substituted or unsubstituted ($C_1$–$C_8$)-alkyl, $C_2$–$C_8$)-alkenyl, ($C_2$–$C_8$)-alkynyl, ($C_1$–$C_8$)-alkoxy, ($C_2$–$C_8$)-alkoxyalkyl, wherein the substituents are selected from the group consisting of mono- or poly-halogens and radicals containing N, O, P atoms,
saturated or unsaturated substituted or unsubstituted ($C_3$–$C_7$)-cycloalkyl, wherein the substituents are selected from the group consisting of linear or branched ($C_1$–$C_8$)-alkyl, ($C_2$–$C_8$)-alkenyl, ($C_1$–$C_8$)-alkoxy, ($C_2$–$C_8$)-alkoxyalkyl, halogens and radicals containing N, O, P atoms,
saturated or unsaturated substituted or unsubstituted ($C_3$–$C_7$)-hetero-cycloalkyl, wherein the substituents are selected from the group consisting of linear or branched ($C_1$–$C_8$)-alkyl, ($C_2$–$C_8$)-alkenyl, ($C_1$–$C_8$)-alkoxy, ($C_2$–$C_8$)-alkoxyalkyl, halogens and radicals containing N, O, P atoms, wherein the hetero moieties in said cycloalkyl groups are selected from the group consisting of N, O, P atoms,
mono and poly substituted and unsubstituted aryl, aralkyl, heteroaryl, heteroaralkyl, wherein the substituents are selected from the group consisting of linear or branched ($C_1$–$C_8$)-alkyl, ($C_2$–$C_8$)-alkenyl, ($C_1$–$C_8$)-alkoxy, ($C_2$–$C_8$)-alkoxyalkyl, halogens and radicals containing N, O, P atoms,
provided however that $R^1$ and $R^2$ when bonded together as shown in phantom and taken together with the carbon atom to which both are linked form a mono or poly substituted or unsubstituted 3- to 7-membered carboxcyclic or heterocyclic, saturated or unsaturated ring, wherein the substituents are selected from the group consisting of linear or branched ($C_1$–$C_8$)-alkyl, ($C_2$–$C_8$)-alkenyl, ($C_1$–$C_8$)-alkoxy, ($C_2$–$C_8$)-alkoxyalkyl, halogens and radicals containing N, O, P atoms,
$R^3$, $R^4$, $R^5$, each independently of the others, have the meanings given for $R^1$, with the proviso that $R^3$ and $R^5$ are not simultaneously other than H and the radicals of the group $R^3$, $R^4$ or $R^5$ are not bonded together to form a ring,
n is an integer from 1 to 3,
which comprises subjecting to oxidising conditions,
a ring compound of the formula II

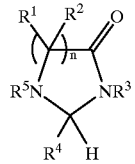

(II)

or a salt thereof.

2. The process of claim 1 wherein the oxidising conditions are those present in an electro-chemical oxidising system.

3. The process of claim 1 wherein the oxidising conditions comprise treating said ring compound of formula II with an oxidising agent selected from the group consisting of an oxidising agent containing active oxygen, a halogen, a halogen containing oxidising agent or a dehydrogenating agent selected from the group consisting of Ru, Rh, Pd, Os, Ir, and Pt.

4. The process of claim 1 wherein aryl is phenyl or naphthyl, aralkyl is benzyl or phenethyl, heteroaryl is furyl, pyrrolyl, pyridyl, heteroaralkyl is furfuryl, pyrrolylmethyl, pyridylmethyl, furylethyl, pyrrolylethyl or pyridylethyl.

5. The process according to claim 1, wherein a compound of formula II is prepared by reacting an α-aminonitrile with an aldehyde.

6. The process according to claim 1, wherein a compound of formula II is prepared by reacting an α-amino acid amide with an aldehyde.

7. The process according to claim 3, wherein the oxidation agent is a halogen.

8. The process according to claim 3, wherein the oxidation agent is a halogen containing oxidising agent.

9. The process according to claim 7, wherein $Cl_2$ is used as the oxidising agent.

10. The process according to claim 3, wherein the oxidising agent is selected from the group of the compounds containing active oxygen.

11. The process according to claim 10, wherein the oxidising agent is a peroxide.

12. The process according to claim 11, wherein the oxidising agent is $H_2O_2$.

13. The process according to claim 1, wherein the oxidation is carried out electrochemically.

14. The process according to claim 2 wherein the oxidation is carried out in the presence of chloride ions.

15. The process according to claim 1, wherein the oxidising agent is a dehydrogenating agent is selected from the group consisting of Ru, Rh, Pd, Os, Ir, and Pt.

16. The process according to claim 15, wherein the dehydrogenating agent is palladium.

17. The process according to claim 1, wherein in of formula II $R^1$, $R^2$ are bonded together as shown in phantom and via the carbon atom to which both are attached form a 5-membered carbocyclic ring, $R^3$, $R^5$ are both H, and $R^4$ is a linear butyl radical.

18. The process according to claim 15, wherein the dehydrogenation is carried out in an organic solvent or organic solvent mixture.

19. The process according to claim 18, wherein the dehydrogenation is carried out in a ketone.

20. The process according to claim 19, wherein the dehydrogenation is carried out in methyl isobutyl ketone.

21. The process according to claim 20, wherein the operation is carried out in a temperature range of from 50° C. to 250° C.

22. The process according to claim 21, wherein the operation is carried out in a temperature range of from 90° C. to 180° C.

23. The process according to claim 15, wherein from 0.1 wt. % to 10 wt. % of metal are used as catalyst, based on the weight of the compound to be dehydrogenated.

24. The process according to claim 23, wherein from 5 wt. % to 7 wt. % of catalyst are used.

25. The process according to claim 1, wherein the cyclic 4-oxoamidine is prepared in the form of its hydrochloride.

* * * * *